United States Patent [19]

Rowsell et al.

[11] 4,032,661
[45] June 28, 1977

[54] CYCLIC SULPHOXIDES AND SULPHONES HAVING A PHYSIOLOGICAL COOLING ACTION ON THE HUMAN BODY

[75] Inventors: David G. Rowsell, Staines; David J. Spring, Datchet, both of England

[73] Assignee: Wilkinson Sword Limited, London, England

[22] Filed: July 20, 1973

[21] Appl. No.: 381,096

[30] Foreign Application Priority Data

July 20, 1972 United Kingdom ............. 33994/72

[52] U.S. Cl. .......................... 424/337; 260/607 A; 424/27; 424/49; 424/73
[51] Int. Cl.² ....................................... A61K 31/10
[58] Field of Search ................ 424/337; 260/607 A

[56] References Cited
UNITED STATES PATENTS

| 2,870,215 | 1/1959 | Davis et al. ..................... 260/607 A |
| 3,304,323 | 2/1967 | Fonken et al. ................. 260/607 A |
| 3,644,442 | 2/1972 | Grimm et al. .................. 260/607 A |
| 3,644,653 | 2/1972 | Tcheiltcheff ....................... 424/358 |

OTHER PUBLICATIONS

Remington's Pharmaceutical Sciences, 1965, 13th Edition, p. 855.
Wilson et al., Textbook of Organic Medicinal and Pharm. Chem. 4th Ed., 1962, pp. 111-112.
Chemical Abstracts 7th Collective Index (1962–1966), (vol. 56–65), pp. 13780s–13782s.
Chemical Abstracts 8th Collective Index (1967–1971), vols. 66–75, pp. 18623s–18627s.

Primary Examiner—Norman A. Drezin
Attorney, Agent, or Firm—Leydig, Voit, Osann, Mayer & Holt, Ltd.

[57] ABSTRACT

Compounds and compositions are disclosed having a physiological cooling action on the skin. The compositions contain as the active ingredient certain cyclic sulphoxides and sulphones.

2 Claims, No Drawings

CYCLIC SULPHOXIDES AND SULPHONES HAVING A PHYSIOLOGICAL COOLING ACTION ON THE HUMAN BODY

FIELD OF INVENTION

This invention relates to topical and other compositions having a physiological cooling effect on the skin and on the mucous membranes of the body, particularly the nose, mouth, throat and gastro-intestinal tract.

BACKGROUND OF THE INVENTION

Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes, etc. and as a component in a wide range of toiletries, liniments and lotions for topical application. Menthol is also a well known tobacco additive for producing a "cool" sensation in the mouth when smoking.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, is circumscribed by its strong minty odour and its relative volatility.

Other compounds have been mentioned in the art as having a physiological cooling effect e.g. 2,4,6-trimethyl-4-heptanol (Parfums-Cosmetiques-Savons, May 1956, pages 17–20) and N,N-diethyl-2-ethylbutanamide (French Pat. No. 1,572,332).

OBJECTS OF INVENTION

The object of the present invention is to provide other compounds having a physiological cooling effect similar to that obtained with menthol but without its attendant disadvantages.

It is a further object of the invention to provide ingestible, topical and other compositions containing such compounds in an amount to provide a physiological cooling effect when such compositions are used in or by the human body.

It is a further object to provide a method of stimulating the cold receptors of the body using agents other than menthol.

SUMMARY OF INVENTION

According to the invention we have found a group of cyclic sulphones and sulphoxides which are capable of stimulating the cold receptors of the nervous system of the body.

DETAILED DESCRIPTION OF INVENTION

The compounds having this physiological cooling effect and usable according to this invention are cyclic sulphoxides and sulphones of the formula:

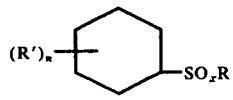

where R is an alkyl radical optionally containing hydroxy, carboxy or carboxyalkyl substituents, R' is $C_1$–$C_5$ alkyl, $x$ is 1 or 2 and $n$ is 0 or an integer of from 1–4 inclusive, it being provided that the total number of carbon atoms provided by the R and R' groups together is in the range 2–12 inclusive, preferably from 5–11 inclusive.

Preferred compounds are those where $n$ has a value of 1 or 2, R' is $C_1$–$C_5$ alkyl and R is $C_1$–$C_5$ alkyl or hydroxyalkyl, or alkylcarboxyalkyl of up to 6 carbon atoms.

Generally speaking the sulphoxides, i.e. compounds where $x$ is 1, are to be preferred over the corresponding sulphones, i.e. the compounds where $n$ is 2.

Particularly preferred compounds made and used according to this invention are p-menth-3-yl n-butyl sulphoxide, n-butyl 1-isobutylcyclohexyl sulphoxide, n-hexyl 1-isobutylcyclohexyl sulphoxide, n-butyl 1-isoamylcyclohexyl sulphoxide and n-hexyl 1,2-diethylcyclohexyl sulphoxide.

The invention therefore provides compositions, in particular ingestible compositions and compositions for topical application, capable of stimulating the cold receptors of the nervous system of the human body comprising an effective amount of a cold receptor stimulant and a carrier therefor, the stimulant comprising one or more of the above defined sulphoxides or sulphones.

The sulphoxides and sulphones of the invention may be readily prepared by conventional methods, such as by the oxidation of the corresponding sulphide, e.g. with hydrogen peroxide in glacial acetic acid.

Many of the compounds of this invention exhibit both geometric and optical isomerism and, depending on the starting materials and the methods used, the compounds of this invention may be isomerically pure, i.e. consisting of one geometric or optical isomer, or they may be isomeric mixtures, both in the geometric and optical sense. Generally speaking the compounds will be used as a mixture of optical and/or geometric isomers, but in some cases the degree of cooling produced by the compounds will differ as between isomers, in which case one or other isomer will be preferred.

The compounds of this invention find utility as additives for a wide variety of compositions for consumption by or application to the human body, i.e., as additives for consumer products which are prepared for a human body use. Broadly speaking, these compositions can be divided into comestible and topical compositions, both terms being taken in their broadest possible sense. Thus comestible is to be taken as including not only foodstuffs and beverages taken into the mouth and swallowed, but also other orally ingested compositions taken for reasons other than their nutritional value, e.g. indigestion tablets, antacid preparations, laxatives etc. Comestible compositions are also to be taken to include edible compositions taken by mouth, but not necessarily swallowed, e.g. chewing gum. Topical compositions are to be taken as including not only compositions such as perfumes, powders and other toiletries, lotions, liniments, oils and ointments applied to the external surfaces of the human body, whether for medical or other reasons, but also compositions applied to, or which, in normal usage, come in contact with, internal mucous membranes of the body, such as those of the nose, mouth, or throat, whether by direct or indirect application or inhalation, and thus include nasal and throat sprays, dentifrice, mouthwash and gargle compositions. Topical compositions are also to be taken to include toilet articles such as cleansing tissues and toothpicks.

A further class of compositions included within the scope of this invention are tobacco and associated articles e.g. pipe and cigarette filters, especially filter tips for cigarettes.

The compositions of this invention will contain an amount of the sulphone or sulphoxide sufficient to stimulate the cold receptors in the areas of the skin or mucous membrane with which the compositions come into contact and thereby promote the desired cold sensation. The degree and longevity of cooling sensation varies from compound to compound and therefore the quantity of stimulant used in each composition will vary widely. As a guide, it may be said that, with the more active compounds of the invention, a significant cooling sensation is achieved upon application to the skin of as little as 0.05 ml. of a 0.5 weight percent solution of the active ingredient in ethanol. For the less active compounds a significant cooling effect is achieved only with more concentrated solutions, e.g. containing 5.0% by weight or more of the active ingredient.

The physiological cooling effect of compounds usable in this invention was tested by a panel of observers. The observers were asked to assess the cooling effect produced by each compound and give the cooling effect a rating according to an arbitrary scale. The results are given below in Table I, the more stars, the greater the cooling effect.

TABLE I

| | |
|---|---|
| n-hexyl 1-isobutylcyclohexyl sulphoxide | * * * * |
| n-butyl 1-isobutylcyclohexyl sulphoxide | * * * |
| n-butyl 1-isoamylcyclohexyl sulphoxide | * * * |
| p-menth-3-yl n-butyl sulphoxide | * * * |
| n-hexyl 1,2-diethylcyclohexyl sulphoxide | * * * |
| p-menth-3-yl ethyl sulphoxide | * * |
| p-menth-3-yl isopropyl sulphoxide | * * |
| p-menth-3-yl methyl sulphone | * * |
| p-menth-3-yl ethylcarboxymethyl sulphoxide | * * |
| p-menth-3-yl ethylcarboxymethyl sulphone | * * |
| isopropyl 2,5-dimethylcyclohexyl sulphoxide | * * |
| isopropyl 2-methylcyclohexyl sulphoxide | * * |
| n-propyl 2-methylcyclohexyl sulphoxide | * * |
| isopropyl 3-methylcyclohexyl sulphoxide | * * |
| isopropyl 4-methylcyclohexyl sulphoxide | * * |
| 3,3,5-trimethylcyclohexyl sec.-butyl sulphoxide | * |
| p-menth-3-yl methyl sulphoxide | * |
| p-menth-3-yl 2-hydroxyethyl sulphoxide | * |
| p-menth-3-yl isopropyl sulphone | * |
| methyl 2,5-dimethylcyclohexyl sulphoxide | * |
| methyl 2,5-dimethylcyclohexyl sulphone | * |
| isopropyl 2,5-dimethylcyclohexyl sulphone | * |
| methyl 2,6-dimethylcyclohexyl sulphoxide | * |
| methyl 2,6-dimethylcyclohexyl sulphone | * |
| isopropyl 2-methylcyclohexyl sulphone | * |
| n-octyl 2-methylcyclohexyl sulphoxide | * |
| isopropyl 3-methylcyclohexyl sulphoxide | * |
| n-butyl 1-isobutylcyclohexyl sulphone | * |
| isobutyl 2-n-butylcyclohexyl sulphoxide | * |
| n-hexyl 2-n-butylcyclohexyl sulphoxide | * |
| isobutyl 2-n-butylcyclohexyl sulphone | * |
| n-hexyl 2-n-butylcyclohexyl sulphone | * |
| n-butyl 1-isoamylcyclohexyl sulphone | * |
| n-propyl 3,3,5-trimethylcyclohexyl sulphone | * |
| tert-butyl 3,3,5-trimethylcyclohexyl sulphone | * |
| n-hexyl 1,3-dimethylcyclohexyl sulphone | * |
| n-hexyl 1,2-diethylcyclohexyl sulphone | * |
| p-menth-3-yl carboxymethyl sulphoxide | * |

In formulating the compositions of this invention the sulphoxide or sulphone will usually be incorporated into a carrier which may be completely inert or which may be or contain other active ingredients. A wide variety of carriers will be suitable, depending upon the end use of the composition, such carriers including solids, liquids, emulsions, foams and gels. Typical carriers for the sulphoxides and sulphones include aqueous or alcoholic solutions; oils and fats such as hydrocarbon oils, fatty acid esters, long chain alcohols and silicone oils; finely divided solids such as starch or talc; cellulosic materials such as paper tissue, tobacco; low-boiling hydrocarbons and halohydrocarbons used as aerosol propellants; gums and natural or synthetic resins.

In most compositions according to the invention the carrier will be or contain as an adjuvant one or more of the following: an antacid, antiseptic or analgesic, a flavourant, colourant, or odourant, or a surfactant.

The following illustrate the range of compositions into which the compounds of this invention can be incorporated:

1. Edible or potable compositions including alcoholic and nonalcoholic beverages, confectionery, chewing gum; cachous; ice cream; jellies;
2. Toiletries including after shave lotions, shaving soaps, creams and foams, toilet water, deodorants and antiperspirants, "solid colognes", toilet soaps, bath oils and salts, shampoos, hair oils, talcum powders, face creams, hand creams, sunburn lotions, cleansing tissues, dentifrices, toothpicks, mouthwashes, hair tonics, eyedrops;
3. Medicaments including antiseptic ointments, pile ointments, liniments, lotions, decongestants, counter-irritants, cough mixtures, throat lozenges, antacid and indigestion preparations, oral analgesics;
4. Tobacco preparations including cigars, cigarettes, pipe tobacco, chewing tobacco and snuff; tobacco filters, especially filter tips for cigarettes.
5. Miscellaneous compositions such as water soluble adhesive compositions for envelopes, postage stamps, adhesive labels etc.

Particular preparations according to the invention are discussed in more detail below.

EDIBLE AND POTABLE COMPOSITIONS

The edible and potable compositions of this invention will contain the active cooling compound in combination with an edible carrier and usually a flavouring or colouring agent. The particular effect of the compounds of the invention is to create a cool or fresh sensation in the mouth, and in some cases, even in the stomach, and therefore they find particular utility in sugar-based confectionery such as chocolate, boiled sweets, mints and candy, in ice cream and jellies and in chewing gum. The formulation of such confections will be by ordinary techniques and according to conventional recipes and as such forms no part of this invention. The active compound will be added to the recipe at a convenient point and in amount sufficient to produce the desired cooling effect in the final product. As already indicated, the amount will vary depending upon the particular compound, the degree of cooling effect desired and the strength of other flavourants in the recipe. For general guidance, however, amounts in the range 0.05 to 2.5% by weight based on the total composition will be found suitable.

Similar considerations apply to the formulation of beverages. Generally speaking the compounds will find most utility in soft drinks e.g. fruit squashes, lemonade, cola etc., but may also be used in alcoholic beverages.

The amount of compound used will generally be in the range 0.02 to 0.5% by weight based on the total composition.

TOILETRIES

Because of the cooling sensation imparted to the skin, a major utility of the compounds of this invention will be in a wide range of toilet preparations and toilet articles. The particular preparations discussed below are to be taken as exemplary.

A major utility will be in after shave lotions, toilet water etc., where the compound will be used in alcoholic or aqueous alcoholic solution, such solutions usually also containing a perfume or mild antiseptic or both. The amount of sulphoxide or sulphone added to the formulation will usually be in the range 0.1 to 5.0% by weight based on the total composition.

Another field of utility will be in soaps, shampoos, bath oils etc. where the compounds will be used in combination with an oil or fat or a natural or synthetic surfactant e.g. a fatty acid salt or a lauroylsulphate salt, the composition usually also containing an essential oil or perfume. The range of soap compositions will include soaps of all kinds e.g. toilet soaps, shaving soaps, shaving foams etc. Usually the active compound will be added to the formulation in amount of from 0.1 to 5.0% by weight.

A further class of toilet compositions into which the compounds of this invention may be incorporated includes cosmetic creams and emollients, such creams and emollients usually comprising a base emulsion and optionally a range of ingredients such as wax, preservative, perfume, antiseptics, astringents, pigments etc. Also included within this class are lipstick compositions such compositions usually comprising an oil and wax base into which the compound can be incorporated along with the conventional ingredients i.e. pigments, perfumes etc. Once again the formulation of such compositions, apart from the incorporation of the active compound, usually in an amount of from 0.05 to 5.0% by weight, is conventional.

Compositions for oral hygiene containing the cold receptor stimulants of this invention include mouthwash, gargle and dentifrice compositions. The first two may be considered together and will usually comprise an aqueous, alcoholic or aqueous-alcoholic solution of an antiseptic often coloured or flavoured for palatability, to which the compound is added in an amount of from 0.05 to 0.5% by weight.

Dentifrice compositions may be of the solid block, powder, paste or liquid type and will usually comprise a finely divided abrasive or polishing material, e.g. precipitated chalk, silica, magnesium silicate, aluminium hydroxide or other similar materials well known in the art, and a detergent or foaming agent. Optional ingredients which may also be included are flavouring agents and colourants, antiseptics, lubricants, thickeners, emulsifiers or plasticizers. The amount of active compound added in such compositions will generally be from 0.1 to 2.5% by weight based on the total composition.

MEDICAMENTS

Because of their cooling effect on the skin and on the mucous membranes of the mouth, throat and nose and of the gastrointestinal tract the compounds of this invention may be used in a variety of oral medicines, nasal and throat sprays, and topical compositions, particularly where a counter-irritant is required. In particular the compounds of the invention may be formulated into antacid and indigestion remedies, in particular those based on sodium bicarbonate, magnesium oxide, calcium or magnesium carbonate, aluminium or magnesium hydroxide or magnesium trisilicate. In such compositions the compounds will usually be added in an amount of from 0.05 to 1.0% by weight.

The compounds of the invention may also be included in oral analgesic compositions e.g. with acetylsalicylic acid or its salts, and in nasal decongestants e.g. those containing ephedrine

TOBACCO PREPARATIONS

The compounds of this invention may be incorporated directly into tobacco to give a cool effect when smoking but without the attendant strong and characteristic odour which is associated with mentholated tobacco and cigarettes. However, a more advantageous utilisation of the compounds of this invention is in pipe or cigarette filters, in particular, filter tipped cigarettes. The pad of filter material, which may be of any of the well known types e.g. cellulose acetate, paper, cotton α-cellulose or asbestos fiber, is simply impregnated with an alcoholic solution of the sulphone or sulphoxide and dried to deposit the compound in the filter pad. The effect is to give a pleasant cool sensation in the mouth when the cigarette is smoked. As little as 0.05 mg. of the compound is effective.

Compositions according to the invention are illustrated by the following Examples.

EXAMPLE 1

After Shave Lotion

An after shave lotion was prepared according to the following recipe by dissolution of the ingredients in the liquid and cooling and filtering:

| Denatured Ethanol | 75% |
|---|---|
| Diethylphthalate | 1.0% |
| Propylene Glycol | 1.0% |
| Lactic Acid | 1.0% |
| Perfume | 3.0% |
| Water | to 100. |

Into separate samples of the base lotion were added 2.0% by weight based on the weight of the sample of p-menth-3-yl methyl sulphoxide and p-menth-3-yl methyl sulphone.

When the final solutions were applied to the face a clearly noticeable cooling effect became apparent after a short interval of time.

EXAMPLE 2

Toilet Water

A toilet water was prepared according to the following recipe:

| Denatured Ethanol | 75.0% |
|---|---|
| Perfume | 5.0% |
| Water | to 100% |

To the recipe was added 3.0%, based on the total composition, of p-menth-3-yl isopropyl sulphoxide.

As with the after shave lotion, a cooling effect was clearly noticeable on the skin well after the termination of any cooling effect attributable to the evaporation of the alcoholic carrier.

EXAMPLE 3

Eye Lotion

An eye lotion was prepared containing the following ingredients:

| | |
|---|---|
| Witch Hazel | 12.95% |
| Boric Acid | 2.00% |
| Sodium Borate | 0.50% |
| Allantoin | 0.05% |
| Salicylic Acid | 0.025% |
| Chlorobutol | 0.02% |
| Zinc Sulphate | 0.004% |
| Water | to 100% |

To the formulation was added 0.005%, based on the total composition, of ethylcarboxymethyl-p-menth-3-yl sulphoxide. When used to bathe the eyes a cool fresh sensation is apparent on the eyeball and eyelids.

EXAMPLE 4

Antiseptic Ointment

An ointment was prepared according to the following formulation:

| | |
|---|---|
| Cetyltrimethyl ammonium bromide | 4.0% |
| Cetyl Alcohol | 6.0% |
| Stearyl Alcohol | 6.0% |
| White Paraffin | 14.0% |
| Mineral Oil | 21.0% |
| Water | to 100% |

The ingredients were mixed, warmed to 40° C and emulsified in a high speed blender. Added to the mixture during blending was 3.0% of 3-methylcyclohexyl isopropyl sulphoxide.

The final ointment when applied to the skin gave rise to a cooling effect.

EXAMPLE 5

Antipruritic Ointment

The following ingredients were warmed together to form a homogenous melt:

| | |
|---|---|
| Methyl salicylate | 50.0% |
| White Beeswax | 25.0% |
| Anhydrous lanolin | 25.0% |

To the melt was added 3.0% of n-butyl 1-isoamylcyclohexyl sulphoxide and the mixture then allowed to solidify. A soft ointment resulted having a soothing effect on the skin accompanied by a cooling effect.

EXAMPLE 6

Cleansing Tissue

A cleansing liquid was prepared having the formulation:

| | |
|---|---|
| Triethanolamine Lauryl sulphate | 1.0% |
| Glycerol | 2.0% |
| Perfume | .95% |
| Water | to 100% |

To this liquid was added 3.0% of 2,5-dimethylcyclohexyl methyl sulphoxide. A paper tissue was then soaked in the liquid.

When the impregnated tissue was used to wipe the skin a fresh cool sensation developed on the skin after a short interval.

EXAMPLE 7

Cigarette Tobacco

A proprietary brand of cigarette tobacco was sprayed with an ethanolic solution of p-menth-3-yl methyl sulphoxide and was rolled into cigarettes each containing approximately 0.05 mg. of active compound. Smoking the impregnated cigarettes produced a cool effect in the mouth characteristic of mentholated cigarettes but without any attendant odour other than that normally associated with tobacco.

Impregnation of the filter tip of a proprietary brand of tipped cigarette with 0.01 mg. of p-menth-3-yl methyl sulphoxide produced a similar effect.

EXAMPLE 8

Toothpaste

The following ingredients were mixed in a blender:

| | |
|---|---|
| Dicalcium phosphate | 48.0% |
| Sodium lauryl sulphate | 2.5% |
| Glycerol | 24.8% |
| Sodium carboxymethyl cellulose | 2.0% |
| Citrus flavourant | 1.0% |
| Sodium saccharin | 0.5% |
| Water | to 100% |

Shortly before completion of the blending operation 0.5% by weight of p-menth-3-yl isopropyl sulphoxide was added to the blender.

When applied as a toothpaste a pleasant cooling effect is noticed in the mouth.

EXAMPLE 9

Aerosol Shaving Soap

An aerosol shaving soap composition was formulated according to the following recipe:

| | |
|---|---|
| Stearic Acid | 6.3% |
| Lauric Acid | 2.7% |
| Triethanolamine | 4.6% |
| Sodium Carboxymethyl Cellulose | 0.1% |
| Sorbitol | 5.0% |
| Water | to 100% |
| Perfume | 0.5% |

The composition was prepared by fusing the acids in water, adding the triethanolamine, cooling and adding the other constituents. To the mixture was then added 0.5% of n-hexyl 1,2-diethylcyclohexyl sulphoxide. The composition was then packaged in an aerosol dispenser under pressure of a butane propellant.

EXAMPLE 10

Deodorant Composition

A deodorant composition suitable for formulation and dispensing as an aerosol under pressure of a suitable propellant was formulated according to the following recipe:

| Denatured ethanol | 96.9% |
|---|---|
| Hexachlorophene | 2.0% |
| Isopropyl myristate | 1.0% |
| Perfume | 0.1% |

To the composition was added 4% by weight of p-menth-3-yl methyl sulphone. Application of the final composition gave rise to a definite cooling sensation on the skin.

EXAMPLE 11

Hair Shampoo

Sodium lauryl ether sulphate, 10 g, was dispersed in 90 g water in a high speed mill. To the dispersion was added 4.5% by weight of p-menth-3-yl n-butyl sulphoxide. When the hair is washed using the shampoo a fresh, cool sensation is noticed on the scalp.

EXAMPLE 12

Solid Cologne

A solid cologne was formulated according to the following recipe:

| Denatured ethanol | 74.5% |
|---|---|
| Propylene Glycol | 3.0% |
| Sodium Stearate | 5.0% |
| Perfume | 5.0% |
| Water | to 100% |

The sodium stearate was dissolved by stirring in a warm mixture of the ethanol, propylene glycol and water. To the solution was added the perfume and 4.0% of n-butyl 1-isobutylcyclohexyl sulphoxide and the mixture then allowed to solidify into a waxy cake.

When applied to the forehead a distinct cooling effect is noticeable.

EXAMPLE 13

Mouthwash

A concentrated mouthwash composition was prepared according to the following recipe:

| Ethanol | 3.0% |
|---|---|
| Borax | 2.0% |
| Sodium Bicarbonate | 1.0% |
| Glycerol | 10.0% |
| Flavourant | 0.4% |
| Thymol | 0.03% |
| Water | to 100% |

To the composition was added 0.2% of isopropyl 4-methylcyclohexyl sulphoxide.

When diluted with approximately 10 times its own volume of water and used to rinse the mouth a cooling effect is obtained in the mouth.

EXAMPLE 14

Soft Drink

A soft drink concentrate was prepared from the following recipe:

| Pure orange juice | 60% |
|---|---|
| Sucrose | 10% |
| Saccharin | 0.2% |
| Orange flavouring | 0.1% |
| Citric acid | 0.2% |

| Sulphur dioxide | trace amount |
|---|---|
| Water | to 100% |

To the concentrate was added 0.05% of 2,5-dimethylcyclohexyl isopropyl sulphoxide.

The concentrate was diluted with water and tasted. An orange flavour having a pleasantly cool after-effect was obtained.

EXAMPLE 15

Boiled Sweet 99.5% sucrose and 0.5% citric acid were carefully fused together in the presence of a trace of water. Just before casting the melt onto a chilled plate 0.1% of p-menth-3-yl ethyl sulphoxide was rapidly stirred in. The melt was then cast. A boiled sweet resulted having a marked cooling effect on the mouth.

EXAMPLE 16

Indigestion Tablet

The following ingredients were ground together:

| Magnesium carbonate | 49.5% |
|---|---|
| Sorbitol | 49.4% |
| Saccharin | 0.1% |
| Talc | 1.0% |

Added to the mixture during grinding was 0.1% of methyl 2,6-dimethylcyclohexyl sulphoxide. After mixing the mixture was pressed into 0.5 g tablets.

Taken by mouth and swallowed the tablets produced, after a short interval of time, a noticeable cooling effect in the stomach.

EXAMPLE 17

Hydrophilic Ointment

A hydrophilic ointment was prepared having the following formulation:

| Propylene Glycol | 12% |
|---|---|
| 1-Octadecanol | 25% |
| White Soft Paraffin | 25% |
| Sodium Lauryl Sulphate | 1% |
| Water | to 100% |

The sodium lauryl sulphate was added to the water and heated to 60° C. The paraffin was melted by heating to 60° C and was then added to the sodium lauryl sulphate mixture with stirring. Propylene glycol and 1-octadecanol were added to this mixture.

To the resultant mixture was added 3% of n-hexyl 1-isobutylcyclohexyl sulphoxide. The final ointment when applied to the skin gave rise to a marked cooling effect.

EXAMPLE 18

Liniment

A liniment was prepared according to the following formulation:

| Methyl salicylate | 25% |
|---|---|
| Eucalyptus Oil | 10% |

| | |
|---|---|
| Arachis Oil | to 100% |

To the composition was added 3% of 3,3,5-trimethylcyclohexyl sec. butyl sulphoxide.

When the final composition was applied to the skin a clearly noticeable cooling effect became apparent after a short interval of time.

EXAMPLE 19

Toothpick

The tip of a wooden toothpick was impregnated with a alcoholic solution containing p-menth-3-yl ethylcarboxymethyl sulphoxide in an amount sufficient to deposit on the toothpick 0.05 mg. of the compound. The toothpick was then dried.

When placed against the tongue a cool sensation is noticed after a short period of time.

The above Examples illustrate the range of compounds and the range of compositions included in the invention. However, they are not to be taken as limiting the scope of the invention in any way. Other compounds within the general formula will be equally suitable for use in the compositions of Examples 1–19 and the physiological effect obtained with the compounds of the invention will recommend their use in a wide variety of other compositions where the cooling effect will be of value.

In addition to the foregoing, the present invention also provides as novel compounds cyclic sulphoxides and sulphones of the formula:

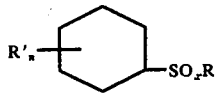

where
R is alkyl, preferably $C_1$–$C_5$ alkyl;
R' is $C_1$–$C_5$ alkyl;
$n$ is 0 or an integer of from 1–4 inclusive; and
$x$ is 1 or 2;
R and R' together providing a total of from 5–12 carbon atoms.

Of especial interest as novel compounds are those of the formula:

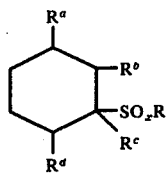

where R and x are as above defined, $R^a$, $R^b$, $R^c$ and $R^d$ each being H or $C_1$–$C_5$ alkyl, with the proviso that at least one is alkyl and at least two are hydrogen.

The novel compounds may be prepared, as hereinbefore indicated, by oxidation of the corresponding sulphides, for example, using hydrogen peroxide and glacial acetic acid.

Compounds of this invention are illustrated by the following Examples. All temperatures are given in degrees Centigrade.

EXAMPLE 20

Part A — Preparation of p-Menth-3-yl methyl sulphide p-Menthane-3-thiol (3.5 g., 20 mmole), methyl iodide (3.5 g., 25 mmole) and sodium ethoxide in ethanol (25 ml. of 0.8 M solution) were mixed together and stirred at room temperature for 2½ hours. The ethanol was then removed and water was added to the residue, which was extracted with ether. The ether extracts were dried (MgSO$_4$) and the solvent was removed. The residue was eluted with 40/60 petroleum ether down a silica column and the product was distilled to give p-menth-3-yl methyl sulphide b.p. 83°–5°/0.05 mm.

Part B — Preparation of p-Menth-3-yl methyl sulphoxide p-Menth-3-yl methyl sulphide, prepared as in Part A (1.5 g., 8 mmoles, hydrogen peroxide (1 ml. of 30% solution) and glacial acetic acid (25 ml.) were stirred at room temperature for 17 hours. The mixture was then poured into ferrous sulphate solution and extracted with ether. The ether extracts were washed with sodium carbonate solution and then dried (MgSO$_4$). Removal of the solvent left an oil which was purified by column chromatography and distillation to give p-menth-3-yl methyl sulphoxide, b.p. 88°/0.03 mm. (Found C, 65.3; H, 10.9. $C_{11}H_{22}OS$ requires C, 65.4; H, 10.9%).

EXAMPLE 21

Preparation of p-Menth-3-yl methyl sulphone p-Menth-3-yl sulphide, prepared as in Part A of Example 20 (1.9 g., 10 mmoles) hydrogen peroxide (3.4 ml. of 30% solution) and glacial acetic acid (25 ml.) were heated together for 3 hours at 70°. After cooling the mixture was poured into ferrous sulphate solution and extracted with ether. The ether extracts were washed with sodium carbonate solution, sodium hydroxide solution and then dried (MgSO$_4$). Removal of the solvent left an oil which was distilled to give p-menth-3-yl methyl sulphone, b.p. 107°–8°/0.05 mm.

Following the procedures of Examples 20 and 21 the following were also prepared:

1. p-Menth-3-yl ethyl sulphoxide
    Found: C, 66.6; H, 11.1. $C_{12}H_{24}OS$ requires C, 66.7; H, 11.1%).
2. p-Menth-3-yl isopropyl sulphoxide (b.p. 91°–93°/0.03 mm.Hg)
    (Found: C, 66.5; H, 10.8; $C_{13}H_{26}OS$ requires C, 67.8; H, 11.2).
3. p-Menth-3-yl n-butyl sulphoxide (b.p. 115°/0.02 mm. Hg)
    Found: C, 68.3; H, 11.6. $C_{14}H_{28}OS$ requires C, 68.8; H, 11.5).

EXAMPLE 22

Part A, Preparation of 2,5-dimethylcyclohexyl isopropyl sulphide

A solution of N NaOEt in ethanol (50 ml.), was added dropwise to a stirred solution of 2,5-dimethylcyclohexyl mercaptan (4.5 g.) and isopropyl iodide (6 g.) in ethanol (15 ml.). The mixture was stirred at room temperature for 3 hours and refluxed for 1 hour. The ethanol was removed in a rotary evaporator and 2N HCl added to the residue. This was extracted twice with ether and the combined extracts dried (MgSO$_4$). Removal of the ether left a yellow oil (6 g.) which g.l.c. indicated to be almost pure 2,5-dimethylcyclohexyl isopropyl sulphide.

Part B — Preparation of 2,5-dimethylcyclohexyl isopropyl sulphoxide

Hydrogen peroxide (2.1 ml. of 30%, 18.3 mmoles) in glacial acetic acid (15 ml.) was added dropwise to a stirred solution of 2,5-dimethylcyclohexyl isopropyl sulphide, prepared as in Part A above (3.4 g., 18.3 mmoles) in glacial acetic acid (25 ml.). Heat was evolved initially and the resulting solution was stirred overnight at room temperature. The reaction mixture was poured into ferrous sulphate solution (800 ml.) and extracted with ether three times. The combined extracts were washed twice with N NaOH solution, water, and then dried (MgSO$_4$). Removal of the solvent left a colourless oil (3.6 g.) which was purified by column chromatography, on silica gel eluting with CHCl$_3$, (the product has a t.l.c. R$_f$ 0.2 on silica gel, eluting with CHCl$_3$) to yield 2,5-dimethylcyclohexyl isopropyl sulphoxide. (Found: C, 65.1; H, 10.8. C$_{11}$H$_{22}$OS requires C, 65.3; H, 10.9%) as a viscous oil which shows a strong S=O stretching frequency at 9.5–9.9 microns in the I.R.

EXAMPLE 23

Preparation of 2,5-dimethylcyclohexyl isopropyl sulphone

A mixture of 2,5-dimethylcyclohexyl isopropyl sulphide, prepared as in Part A of Example 22 (3.4 g.), hydrogen peroxide (8 ml. of 30%) and glacial acetic acid (40 ml.) was heated at reflux for 5 hours. The mixture was worked up as described in Example 22, Part B, and the product purified by column chromatography (R$_f$ 0.5) to yield 2,5-dimethylcyclohexyl isopropyl sulphone. (Found: C, 59.5; H, 10.2. C$_{11}$H$_{22}$O$_2$S requires C, 60.6; H, 10.1%) as a viscous colourless oil which shows strong S=O stretching absorptions at 7.7–7.8 and 8.8–9.0 microns in the I.R.

EXAMPLE 24

Part A — Preparation of n-Hexyl 1,2-diethylcyclohexyl sulphide

To a cooled (0° C) mixture of water (13 ml.) and 27 mg. concentrated sulphuric acid was added dropwise 1,2-diethylcyclohexanol (12 g., 77 mmole) and then n-hexylthiol (9.1 g., 77 mmole). The mixture was stirred at 0° C for 6 hours and at room temperature for 1 hour. The mixture was then poured into 1 liter of cold water and extracted with ether. The ether extract was washed with 2N sodium hydroxide and water and dried (MgSO$_4$). The solvent was removed by distillation and the residue was distilled under reduced pressure to give n-hexyl 1,2-diethylcyclohexyl sulphide (15 g.) as a colourless liquid, b.p. 110°–4°/0.03 mm.

Part B — Preparation of n-Hexyl 1,2-diethylcyclohexyl sulphoxide

A mixture of n-hexyl 1,2-diethylcyclohexyl sulphide (6.5 g., 25 mmoles), glacial acetic acid (50 ml.) and hydrogen peroxide (2.7 ml. of 100 vols.) was stirred at room temperature for 20 hours. The mixture was poured into an excess of 2N sodium hydroxide and extracted with methylene chloride. The extract was washed with water and dried (MgSO$_4$). The solvent was removed and the residual oil (6 g.) was eluted with chloroform from a silica column (Merck Kieselgel 7734). n-Hexyl 1,2-diethylcyclohexyl sulphoxide was obtained as a viscous liquid (Found: S = 11.7%. C$_{16}$H$_{32}$OS requires S = 11.8%).

Following the procedures of Example 24 the following were also prepared:

1. n-Butyl 1-isobutylcyclohexyl sulphoxide
   (Found: C, 67.8; H, 11.8. C$_{14}$H$_{28}$OS requires: C, 68.8; H, 11.4%.
2. n-Butyl 1-isoamylcyclohexyl sulphoxide
   (Found: C, 68.1; H, 11.8. C$_{15}$H$_{30}$OS requires: C, 69.8; H, 11.6%).

We claim:

1. In a manufactured consumer product for topical application to the human body, comprising a topically administrable carrier, and, as adjuvants in said carrier, i] an antiseptic or perfume or both, and ii] a compound capable of stimulating the cold receptors of the nervous system of the surface tissues of the body when brought into contact therewith by topical application of the said product, the improvement which comprises using as said cold receptor stimulating compound, an effective amount of a cold receptor stimulating sulfoxide or sulfone of the formula:

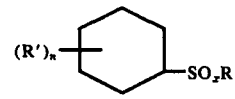

where
R is C$_1$–C$_5$ alkyl;
R' is C$_1$–C$_5$ alkyl;
n is 1 or 2;
the total number of carbon atoms provided by R and all the R' groups is from 2–12 inclusive; and
x is 1 or 2.

2. A method of stimulating the cold receptors of the nervous system of the surface tissues of the body, which comprises applying thereto by topical application in a topically administrable carrier, an effective amount of a cold receptor stimulating sulfoxide or sulfone of the formula defined in claim 1.

* * * * *